United States Patent [19]
Buckle et al.

[11] 3,984,565
[45] Oct. 5, 1976

[54] ACETOPHENONE DERIVATIVES

[75] Inventors: Derek Richard Buckle, Redhill; Harry Smith, Maplehurst, near Horsham; Barrie Christian Charles Cantello, Horsham, all of England

[73] Assignee: Beecham Group Limited, Great Britain

[22] Filed: Jan. 16, 1975

[21] Appl. No.: 541,421

Related U.S. Application Data

[62] Division of Ser. No. 454,922, March 26, 1974.

[30] Foreign Application Priority Data

Apr. 3, 1973  United Kingdom............... 15882/73

[52] U.S. Cl.............................. 424/279; 424/309; 424/317
[51] Int. Cl.²..................................... A61K 31/335
[58] Field of Search.................... 424/317, 309, 279

[56] References Cited
UNITED STATES PATENTS

| | | | |
|---|---|---|---|
| 3,864,493 | 2/1975 | Cairns et al.................... | 424/283 |
| 3,879,544 | 4/1975 | Reisner et al.................. | 424/337 |
| 3,883,653 | 5/1975 | Barth............................. | 424/251 |
| 3,885,038 | 5/1975 | Pfister et al.................... | 424/283 |

*Primary Examiner*—Norman A. Drezin

[57] ABSTRACT

A pharmaceutical composition is produced which is useful for treating allergic conditions in humans which comprises an anti-allergenic amount of a compound of the formula:

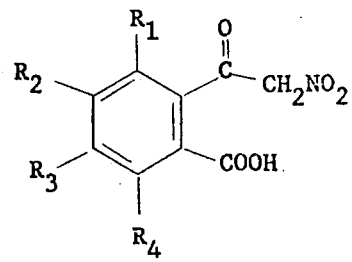

or a pharmaceutically acceptable salt or ester thereof, wherein $R_1$, $R_2$, $R_3$ and $R_4$ are the same or different and each is hydrogen, alkyl, alkoxy, aryl, aralkyl or halogen or any two of $R_1$, $R_2$, $R_3$ and $R_4$ taken together, with the carbon atoms to which they are attached, form a phenyl, cyclohexyl or cyclohexenyl ring, in combination with a pharmaceutically acceptable carrier.

63 Claims, No Drawings

ACETOPHENONE DERIVATIVES

This is a division of application Ser. No. 454,922 filed Mar. 26, 1974.

This invention relates to pharmaceutical compositions which are useful in the inhibition of the effects of certain types of antigen-antibody reactions, and are therefore of the value in the prophylaxis and treatment of diseases associated with allergic or immunological reactions, e.g. certain types of asthma and hay-fever and also in the treatment of rhinitis. The invention also includes a number of new substituted ω-nitroacetophenones and a method for their preparation, as well as intermediates useful in their preparation.

We have discovered that certain derivatives of ω-nitroacetophenone have useful activity in warm-blooded mammals in that they inhibit the effects of certain types of antigen-antibody reactions. The class of ω-nitroacetophenones which we have found to be active in this way has formula (I):

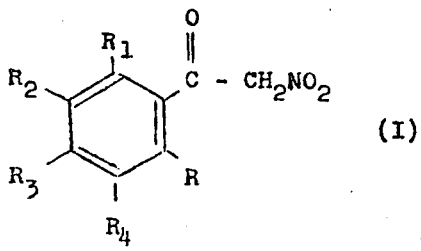

and the salts of compounds (I) are also active. In formula (I) the group R is a carboxylic acid group or a salt or ester derivative of a carboxylic acid group; $R_1$, $R_2$, $R_3$ and $R_4$ are each hydrogen or alkyl, alkoxy, aryl, aralkyl, heterocyclic or halogen groups, or any two of the groups $R_1$, $R_2$, $R_3$ and $R_4$ taken together represent the residue of a substituted or unsubstituted carbocyclic or heterocyclic ring system. However, a search of the chemical literature has revealed that not all the members of class (I) are novel compounds. Below we list some of the compounds of formula (I) which are mentioned in the literature together with the appropriate literature reference:

(I)  (R) = —CO$_2$CH$_3$; $R_1 = R_2 = R_3 = R_4 = H$ (J. Gen. Chem [1956], 26, 1039)

(I)  R = —CO$_2$C$_2$H$_5$; $R_1 = R_2 = R_3 = R_4 = H$ (ditto)

(I)  R = —CO$_2$H; $R_1 = R_2 = R_3 = R_4 = H$ (ditto)

R = —CO$_2$ $^{iso}$C$_3$H$_7$ $R_1 = R_2 = R_3 = R_4 = H$ (J. Gen. Chem. [1954] 24, 725)

(I)  R = —CO$_2$$^{iso}$C$_4$H$_9$; $R_1 = R_2 = R_3 = R_4 = H$ (ditto)

Although the compounds have been reported in the literature, no form of useful biological activity has been ascribed to them. Likewise there has been, in the literature, no suggestion that such compounds are likely to possess any form of useful biological activity and in particular the discovery that they have anti-allergic activity has not been predicted in any way.

Accordingly, in its broadest aspect, the present invention provides a pharmaceutical composition comprising a compound of formula (I) or a pharmaceutically acceptable salt or ester thereof:

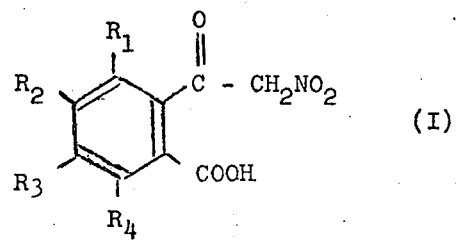

together with one or more pharmaceutically acceptable carriers in which formula $R_1$, $R_2$, $R_3$ and $R_4$ represents hydrogen or lower alkyl, lower alkoxy, aryl, aralkyl, heterocyclic or halogen groups and any two of the groups $R_1$, $R_2$, $R_3$ and $R_4$ when taken together with the carbon atoms to which they are joined complete a carbocyclic or heterocyclic ring system.

Examples of groups $R_1$, $R_2$, $R_3$ and $R_4$ which may be present in compounds (I) are methyl, ethyl, n- and iso-propyl n-, sec-, and tert - butyl, methoxy ethoxy, n- and iso-propoxy, n-, sec- and tert - butoxy, phenyl, benzyl, pyridyl, fluoro, chloro, bromo, or iodo groups. In addition $R_1$ and $R_2$ or $R_2$ and $R_3$ or $R_3$ and $R_4$ taken together may represent the residue of a 1,2, phenylene ring or a 1,2-cyclohexenylene ring which may carry one or more of the substituents listed above.

Examples of suitable esters of compound (I) include simple alkyl, aryl and aralkyl esters such as methyl, ethyl, n- and sec-propyl, n-, sec- and tert - butyl, phenyl, benzyl, indanyl, as well as more complex esters such as acyloxymethyl esters and phthalidyl esters. Examples of suitable salts include the alkali metal salts, particularly potassium and sodium, and the alkaline earth metal salts such as aluminium and magnesium salts, as well as salts with organic bases such as amines or amino compounds. It will also be noted that the acidic methylene group of the CO—CH$_2$—NO$_2$ moiety of (I) permits the formation of salts and any of the previously listed salts can be formed at this reactive centre.

The compositions of this invention may be presented as a microfine powder for insufflation, e.g. as a snuff or in capsules of hard gelatin. They may also be presented with a sterile liquid carrier for injection. In the case of compounds of formula (I) which are active when given by the oral route, the compositions of this invention may be in the form of syrups, tablets, capsules, pills and the like. Preferably the compositions are in unit dosage form, or in a form which the patient can administer to himself a single dosage. If desired, a small amount of a bronchodoilator compound such as isoprenaline may be incorporated into the compositions of this invention both to inhibit the cough response if the composition is insufflated and to provide immediate relief during an asthmatic attack. The effective dose of compound (I) depends on the particular compound employed but is in general in the range of from 0.1 mg/kg/day to 100mg/kg day.

The precise nature of the pharmaceutical carrier used in the compositions of this invention is not important. Standard pharmaceutical practice may be followed.

As is common practice, the compositions will usually be accompanied by written or printed directions for use in the medical treatment concerned, in this case as an anti-allergic agent for prophylaxis or treatment of, for example, asthma, hayfever or rhinitis.

In another of its aspects the present invention provides compounds of formula (I) and pharmaceutically acceptable salts and esters thereof:

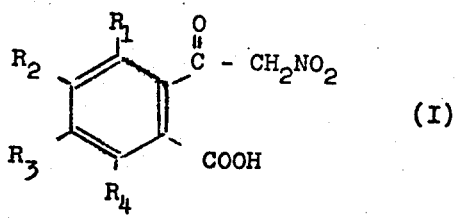

(I)

wherein $R_1$, $R_2$, $R_3$ and $R_4$ are each hydrogen or alkyl, alkoxy, aryl, aralkyl, heterocyclic or halogen groups, or any two of the groups $R_1$, $R_2$, $R_3$ and $R_4$ taken together with the carbon atom to which they are attached complete a carbocyclic or heterocyclic ring, with the exception of the following compounds and salts thereof:

2-Methoxycarbonyl-ω-nitroacetophenone
2-Ethoxycarbonyl-ω-nitroacetophenone
2-Carboxy-ω-nitroacetophenone
2-Isopropoxycarbonyl-ω-nitroacetophenone
2-Isobutoxycarbonyl-ω-nitroacetophenone Hereafter in this specification, when the phrase "the compounds of this invention" is used it is to be understood that we mean compounds of formula (I) and salts and esters thereof, excluding the five compounds specifically listed above, and their salts.

The identities of the various groups $R_1$, $R_2$, $R_3$ and $R_4$ have already been discussed, but specifically preferred compounds of this invention include the following free acids and their salts and esters 4-Ethyl-5-methyl-ω-nitroacetophenone-2-carboxylic acid
4-Methyl-5-ethyl-ω-nitroacetophenone-2-carboxylic acid
4,5-dimethyl-ω-nitroacetophenone-2-carboxylic acid
4,5-diethyl-ω-nitroacetophenone-2-carboxylic acid
4,5-di-n-propyl-ω-nitroacetophenone-2-carboxylic acid Specifically preferred esters of the above three compounds include the methyl and ethyl esters.

It has already been said that the compounds and compositions of this invention show anti-allergic activity. We have some evidence to show that the anti-allergic activity of compounds (I) is at least partly due to the fact that they cyclise in vivo to produce detectable levels of compounds (III)

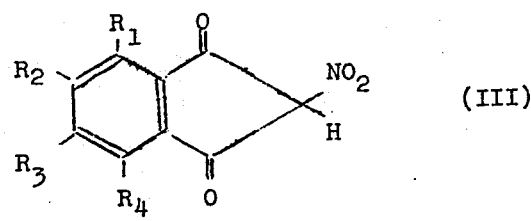

(III)

and compounds (III) are known to have antiallergic activity. This observation however, does not rule out the possibility that compounds (I) have intrinsic activity in their own right, and in any event, the pattern of anti-allergic activity observed in vivo with compounds (I) appears to be different from that of compounds (III). For example, the duration of effect of compounds (I) appears to be more prolonged than compounds (III).

Whatever the mode of action of the compounds of this invention, they are not useful as antiallergic agents in their own right, but as intermediates for chemical conversion into the known antiallergic agents of formula (III). Thus, compounds of formula (I) wherein R is a lower alkyl ester derivative of a carboxylic acid, and $R_1$, $R_2$, $R_3$ and $R_4$ are inert substituents such as lower alkyl groups, may be converted into the corresponding cyclic compounds (III) by reaction with a base, e.g. sodium hydride or sodium. The mechanism of cyclisation is believed to involve the abstraction of a proton from the acidic methylene group in the nitroacetophenone by the base, followed by nucleophilic attack on the esterifed carboxyl group, with elimination of alcohol. For example, lower alkyl esters of 4,5-dimethyl-ω-nitroacetophenone-2 carboxylic acid can be reacted with sodium hydride in a solvent such as toluene to produce 5,6-dimethyl-2-nitroindane-1,3-dione in high yield. Similarly, the 4,5-dimethyl-ω-nitroacetophenone-carboxylic acid lower alkyl esters can be converted to 5,6-dimethyl-2-nitroindane-1,3-dione in high yield. Similarly, the 4,5-diethyl-ω-nitroacetophenone-carboxylic acid lower alkyl esters can be converted to 5,6-diethyl-2-nitroindane-1,3-dione.

It is clear from the above that the nitroacetophenone carboxylic acids, salts and esters of this invention are useful both as anti-allergic compounds in their own right and as precursors for a known series of anti-allergic nitroindanediones. The compounds of this invention (I) may be prepared in a variety of ways. Thus, a compound of formula (III) or a salt thereof:

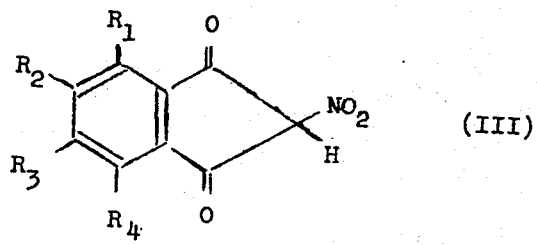

(III)

may be reacted with an alcohol, $R_1$, $R_2$, $R_3$, $R_4$ being as defined with respect to formula (I) and the alcohol being chosen according to the required ester of compound (I), and, if desired, the resulting ester may be de-esterified to produce a free acid of formula (I), and if desired, the resulting free acid may be salified.

The above reaction scheme may be represented as follows:

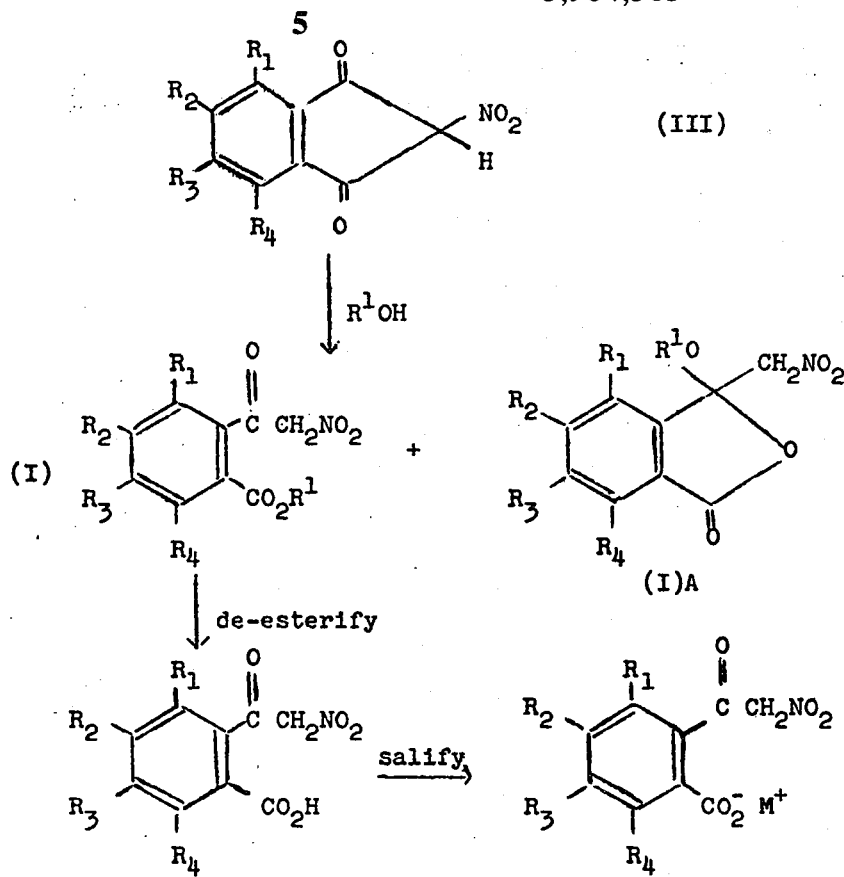

It will be seen that compound (IA) is an unwanted by-product (although as will be apparent later it may be useful as an intermediate for compound (I)) and must be separated from compound (IA). This can be done by the usual techniques such as selective extraction and selective solvent precipitation. Where the substituents $R_1 - R_4$ in starting material (III) are asymmetric two isomers of compound (I) may theoretically be formed e.g.

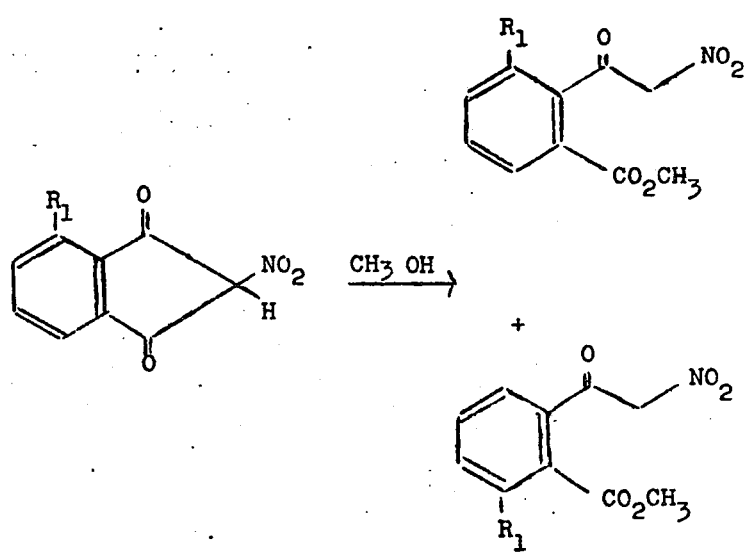

In general one or other of such isomers will predominate and can easily be separated from the other. On occasions, one isomer may predominate to such an extent that the trace amounts of the other isomer need not be separated.

The ester compounds (I) prepared as above may be used as the starting materials for compounds (I) wherein R is a carboxylic acid group. All that is necessary is to de-esterify, using known methods according to the identity of the ester, e.g. hydrolysis, the ester compound (I). For example compounds (I) wherein $R^1$ is a methyl or ethyl group can be converted into the parent acids by alkaline hydrolysis using, for example, sodium hydroxide.

Hydrolysis of the by-product (IA) mentioned above also lends to the formation of the desired compound (I) as a free carboxylic acid. These compounds are hydrolysed by attack of hydroxyl ion at $C_1$, thus:

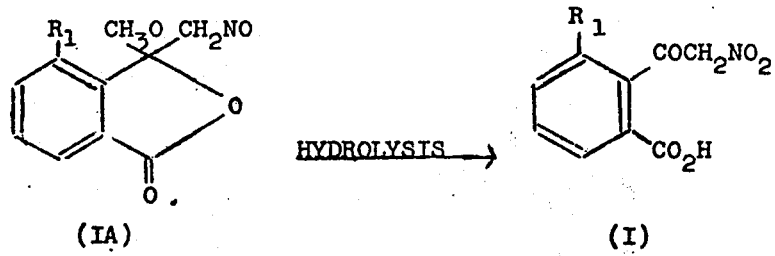

(IA)        (I)

Having prepared, by this method a free acid, it is a simple matter to convert the acid to a salt or ester. Thus, if the desired ester compound (I) is not accessible by alcoholysis of the nitroindanedione (II), it can be prepared by esterification of the parent acid compound (I).

Yet another method of preparing the compounds of this invention involves the reaction of a compound of formula (IV);

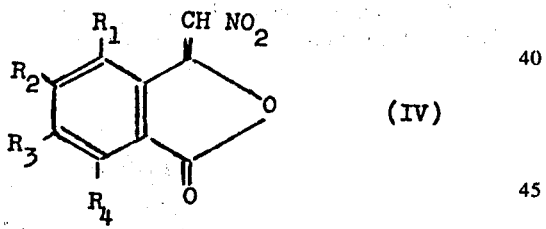

wherein $R_1$, $R_2$, $R_3$, and $R_4$ are as defined with respect to formula (I) with a compound $MOR^1$ wherein M is an alkali metal or alkaline earth metal ion and $R^1$ is the organic residue of an alcohol, thereby producing a compound of formula (IB):

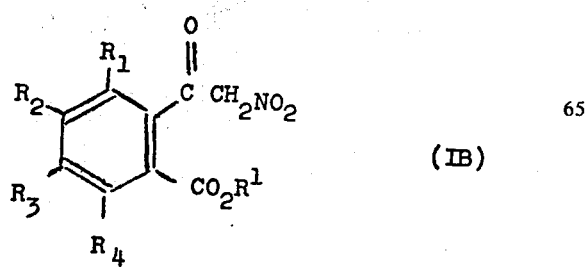

and if desired de-esterifying compound (IB) to produce the free acid and if desired salifying the free acid to produce the desired salt.

The above reaction can be effected for example with an alkali metal or alkaline earth metal alkoxide to produce the alkyl ester (I):

The above reaction may be modified by substituting a hydroxylic base such as sodium or potassium hydroxide for the alkali or alkaline earth metal compound $MOR^1$; in this case the resultant product will usually be the free acid or a salt thereof, which can then be further esterified.

Throughout this specification we have referred to "free acid compounds of formula I" and have implied that these compounds have the following structural formula:

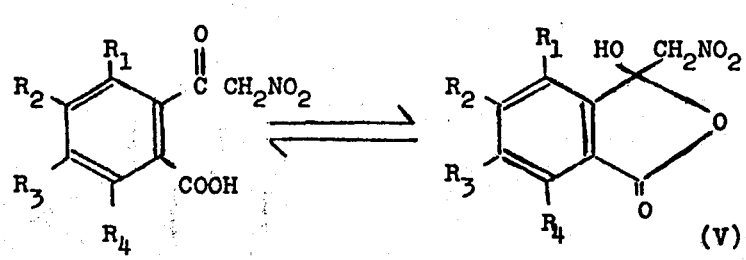

In fact, these free acid compounds tend to be in equilibrium in solution as follows:

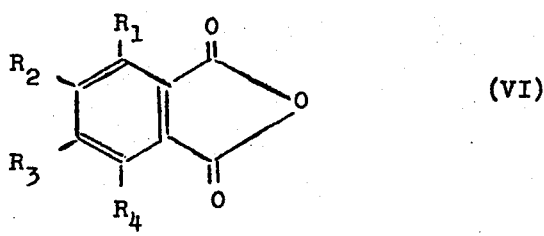

Thus, wherever we have referred to free acids of formula (I) it is to be understood that such compounds may also be in the form of their tautomers (V). These free acids (and their tautomers V) may be prepared directly by a process which comprises the reaction of a compound of formula (VI).

wherein $R_1$, $R_2$, $R_3$ and $R_4$ are as hereinbefore defined, with nitromethane and a base. Suitable bases include the alkali metal or alkaline earth metal alkoxides.

The following Examples illustrate the preparation of compounds of formula (I), their biological activities as revealed in the rat passive cutaneous anaphylaiis test, and their use as intermediates in the preparation of known anti-allergic nitroindanediones.

EXAMPLE 1

A mixture of 2-nitroindane-1,3-dione (22.3g., 0.117 moles) and methanol (100 ml) was heated under reflux for 4 hours, cooled, poured into water (1 liter), allowed to stand overnight then filtered. The solid was extracted with 5% sodium bicarbonate solution (200 ml). The insoluble material was filtered off, dried, and recrystallised from ethanol to give the Ψ-ester, 3-methoxy-3-nitromethylphthalide, m.p. 113°–114°. Acidification of the sodium bicarbonate filtrate, filtration and recrystallisation from ethanol gave the α-methyl ester, 2-methoxycarbonyl-ω-nitroacetophenone, m.p. 108°–9°.

EXAMPLE 2 a. 2-Nitroindane-1,3-dione (20.5g; 0.107 moles) in ethanol (100 ml) was heated under reflux for 4 hours, cooled, poured into water (1 liter), allowed to stand overnight and filtered. The solid was extracted with 5% sodium bicarbonate solution (3 × 100 ml) and filtered. The insoluble solid was predominantly the Ψ-ethyl ester, 3-ethoxy-3-nitromethylphthalide, contaminated with some α-ethyl ester. Acidification of the combined sodium bicarbonate filtrates, filtration and recrystallisation from ethanol gave the α-ethyl ester, 2-ethoxycarbonyl-ω-nitroacetophenone, m.p. 81°.

b. The impure Ψ-ethyl ester from (a) above, was dissolved in a mixture of acetic acid (60 ml.) — nitric acid (8 ml, specific gravity 1.42), allowed to stand for 17 hours, poured into water (200 ml) filtered and the solid recrystallised from methanol to give the Ψ-ethyl ester 3-ethoxy-3-nitromethylphthalide, m.p. 91°–93°.

EXAMPLE 3 a. 5,6-Dimethyl-2-nitroindane-1,3-dione (10.0 g; 0.046 moles) in methanol (50 ml.) was heated under reflux for 4 hours and cooled. Filtration of the precipitate and recrystallisation from methanol gave the α-methyl ester, 2-methoxycarbonyl-4,5-dimethyl-ω-nitroacetophenone, m.p. 139°–139.5°.

b. The filtrate was poured into water (500 ml.), allowed to stand for 2 hours and filtered to give impure Ψ-methyl ester. Treatment of this impure Ψ-methyl ester with acetic acid - nitric acid, as described in Example 2(b) gave pure Ψ-methyl ester, 5,6-dimethyl-3-methoxy-3-nitromethylphthalide m.p. 147°–50° (from ethanol).

c. 3% Sodium methoxide in methanol (20 ml) was added to 5,6-dimethyl-3-methoxy-3-nitromethylphthalide, prepared as in (b) above, (2.0 g) and the mixture stirred at room temperature for 10 minutes. Addition of water (70 ml.), acidification with cold concentrated hydrochloric acid, filtration and recrystallisation from methanol gave 2-methoxycarbonyl-4,5-dimethyl-ω-nitroacetophenone, m.p. 138°–9°.

EXAMPLE 4

5,6-Dimethyl-2-nitroindane-1,3-dione (20.0g) in ethanol (100 ml) was heated under reflux for 3.75 hours and cooled. Filtration and recrystallisation from ethanol gave 2-ethoxycarbonyl-4,5-dimethyl-ω-nitroacetophenone, m.p. 102°–102.5°.

EXAMPLE 5

4,5-dimethyl-2-nitroindane-1,3-dione (5.23g) in n-propanol (25 ml) was heated under reflux for 4 hours and cooled. Filtration and recrystallisation from n-propanol gave 2-n-propoxycarbonyl-4,5-dimethyl-ω-nitroacetophenone m.p. 95–6°.

EXAMPLE 6

5,6-Dimethyl-2-nitroindane-1,3-dione (5.01g) in isopropanol (30 ml) was heated under reflux for 3¾ hours and cooled. Filtration and recrystallisation from isopropanol gave 2-Isopropoxycarbonyl-4,5-dimethyl-ω-nitroacetophenone, m.p. 129°–130°.

EXAMPLE 7 a. 2-Nitro-4-phenylindane-1,3-dione (17.0g; 0.064 mole) in methanol (70 ml) was heated under reflux for 4 hours, and the cooled yellow solution poured into water (70 ml). After standing several hours, a yellow solid formed, which was filtered off and extracted with 5% sodium bicarbonate solution (2 × 400 ml). The residual solid was dissolved in chloroform and extracted once with 5% sodium bicarbonate solution (200 ml). The combined bicarbonate extracts on acidification afforded a mixture of two α-esters, 2-methoxycarbonyl-5-phenyl-ω-nitroacetophenone and 2-methoxycarbonyl-3-phenyl-ω-nitroacetophenone, in a 4 to 1 ratio respectively. Fractional recrystallisation from ethanol afforded the former compound, m.p. 132°C.

b. Evaporation of the chloroform phase afforded a yellow solid which gave the Ψ-ester, 3-methoxy-3-nitromethyl-7-phenylphthalide on recrystallisation from ethanol, m.p. 159°C.

EXAMPLE 8

A mixture of 3-methoxy-3-nitromethylphthalide (3.82g; 0.017 mole) and 5% sodium hydroxide solution (50 ml.) was stirred at room temperature for 40 minutes, filtered, acidified and allowed to stand for 2 hours. The precipitate was filtered off and recrystallised from water to give ω-nitroacetophenone-2-carboxylic acid, m.p. 127°–133°.

EXAMPLE 9

A mixture of 2-methoxycarbonyl-4,5-dimethyl-ω-nitroacetophenone (2.5 g; 0.010 mole) and 5% sodium hydroxide solution (40 ml) was stirred at room temperature for 1 hour, acidified, allowed to stand for 30 minutes. The solid was filtered off and recrystallised from benzene to give 4,5-dimethyl-ω-nitroacetophenone-2-carboxylic acid, m.p. 166°–7°.

EXAMPLE 10

3-Methoxy-3-nitromethyl-7-phenylphthalide (3.5 g; 0.012 mole) was stirred with 5% sodium hydroxide solution (35 ml) until solution was complete and the filtered solution acidified to pH 1. The initially formed gum crystallised on scratching to give a white solid.

Recrystallisation from benzene gave ω-nitro-3-phenylacetophenone-2-carboxylic acid, m.p. 107°C.

EXAMPLE 11

Methanolysis and ethanolysis of 5,6-diethyl-2-nitroindane-1,3-dione, 5-methyl-6-ethyl-2-nitroindane-1,3-dione, 5-ethyl-6-methyl-2-nitroindane-1,3-dione, 5,6-di-n-propyl-2-nitroindane-1,3-dione, 4-methoxy-6-ethyl-2-nitroindane-1,3-dione, 2-nitrobenz[f]indane-1,3-dione and 4-fluoro-2-nitroindane-1,3-dione by the same general procedure as described in examples 1, 2(a), 3(a), 4, 5 and 6 produces the following compounds:

2-methoxycarbonyl-4,5-diethyl-ω-nitroacetophenone
2-ethoxycarbonyl-4,5-diethyl-ω-nitroacetophenone
2-methoxycarbonyl-4-methyl-5-ethyl-ω-nitroacetophenone
2-ethoxycarbonyl-4-methyl-5-ethyl-ω-nitroacetophenone
2-methoxycarbonyl-4-ethyl-5-methyl-ω-nitroacetophenone
2-ethoxycarbonyl-4-ethyl-5-methyl-ω-nitroacetophenone
2-ethoxycarbonyl-4,5-di-n-propyl-ω-nitroacetophenone
2-methoxycarbonyl-4,5-di-n-propyl-ω-nitroacetophenone
2-methoxycarbonyl-3-methoxy-5-ethyl-ω-nitroacetophenone plus the 6,4 isomer.
2-ethoxycarbonyl-3-methoxy-5-ethyl-ω-nitroacetophenone plus the 6,4 isomer
2-methoxycarbonyl-ω-nitrobenz [f] acetophenone
2-ethoxycarbonyl-ω-nitrobenz [f] acetophenone
2-methoxycarbonyl-3-(and-6-) fluoro-ω-nitroacetophenone
2-ethoxycarbonyl-3-(and-6-) fluoro-ω-nitroacetophenone

EXAMPLE 12

Nitromethane (5.2g; 0.086 mole) was added to a suspension of 4,5-dimethyl phthalic anhydride (7.0g; 0.04 mole) in dry ether (850 ml) followed by a solution of sodium (0.9g; 0.04 mole) in dry ethanol (20 ml). A thick precipitate formed which was filtered off after stirring for 6 hours and dissolved in ice-water (150 ml). Acidification with hydrochloric acid gave 4,5-dimethyl phthalic acid mono methyl ester as a white solid which was immediately filtered off. The filtrate on standing overnight deposited 2-carboxy-4,5-dimethyl-ω-nitroacetophenone, m.p. 177°–8°C.

EXAMPLE 13 a. Dicyclohexylcarbodiimide (0.452g; 10% excess) was added in one portion to a cold (10°C) stirred solution of 2-carboxy-4,5-dimethyl-ω-nitroacetophenone (0.474g; 0.002 mole) in dry acetone (15 ml) and the mixture stirred in an ice bath for 2 hours.

The precipitated dicyclohexyl urea was filtered off, saturated with a further 15 ml of acetone and refiltered. Evaporation of the acetone filtrates afforded 5,6-dimethyl-3-nitromethylene phthalide in quantitative yield. (Mixture of cis and trans isomers).

b. A solution of 2-carboxy-4,5-dimethyl-ω-nitroacetophenone (2.37 g; 0.9 mole) in acetic anhydride (15 ml) was refluxed for 10 mins and the solvent removed under reduced pressure. Treatment of the residue with ethanol followed by filtration afforded 5,6-dimethyl-3-nitromethylene phthalide as a yellow crystalline solid, m.p. (acetic acid) 211°–212°C (pure cis isomer with respect to the nitro and aryl groups)

c. 5,6-Dimethyl-3-nitromethylene phthalide (0.003 mole) was added to a methanolic solution of sodium methoxide (0.55 g; 0.01 mole) and the mixture shaken at room temperature. After the colour had disappeared, water (50 ml) was added and 2-methoxycarbonyl-ω-nitroacetophenone m.p. 139°–139.5° (from ethanol) was precipitated.

EXAMPLE 14

Cyclisation of 2-methoxycarbonyl-ω-nitroacetophenone to 2-nitroindane-1,3-dione a. A suspension of 2-methoxycarbonyl-ω-nitroacetophenone (2.23 g; 0.01 mole) in dry benzene (30 ml) was treated with sodium hydride (0.24 g; 0.01 mole) and the mixture heated for 6 hours at 100°C. After cooling, water was added and the phases separated. Acidification of the aqueous phase gave 0.964g of starting material. Evaporation of the aqueous filtrate gave a yellow solid which after recrystallisation gave 2-nitroindandione, m.p. (water; hydrochloric acid) 110°–113°C.

EXAMPLE 15

Cyclisation of 2-Methoxycarbonyl-4,5-dimethyl-ω-nitroacetophenone to 5,6-dimethyl-2-nitroindan-1,3-dione A suspension of 2-methoxycarbonyl-4,5-dimethyl ω-nitroacetophenone (2.15g; 0.01 mole) and sodium hydride (0.24g; 0.01 mole) in dry toluene (30 ml), was refluxed over 4 hours, and worked up as in example 14 to yield 5,6-dimethyl-2-nitro-indan-1,3-dione, m.p. (water, hydrochloric acid) 111°–113°C.

EXAMPLE 16

Biological results

Some of the ω-nitroacetophenones prepared in the preceding Examples were submitted for biological testing. The test system was the Rat Passive Cutaneous Anaphylaxis (PCA) test described below in (ii).

i. Serum containing heat labile homocytotropic antibody was raised in rats by a method similar to that used by Mota. (I. Mota Immunology 1964, 7, 681).

Male Wistar rats of 250–300 g, were injected intraperitoneally with 0.5 ml of *Bordatella pertussis* vaccine (containing 4 × $10^{10}$ dead organism per ml) and subcutaneously with 0.5 ml of an emulsion of 100 mg. of ovalbumin in 2 ml of saline and 3 ml of incomplete Freunds' adjuvant. Rats were bled by cardiac puncture on day 18, the blood was pooled and separated and serum stored at −20° and thawed only once before use.

ii. The P.C.A test was similar to that described by Ovary and Bier (A. Ovary and O. E. Bier, Prod. Soc. Exp. Biol. Med. 1952, 81, 584) and Goose and Blair (J. Goose and AM. J. N Blair, Immunology 1969, 16, 769)

0.1 ml of each of six twofold serial dilutions of the serum in 0.9% saline were injected intradermally into separate sites on the shaved dorsal surface of 250–350 g Wistar rats. 72 hours later the animals were challenged by i.v. injection of 0.3 ml of 1% ovalbumin mixed with 0.1 ml of a 5% solution of pontamine sky blue dye both in isotonic saline buffered with pH. 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the two or three lowest dilutions. Typically, six twofold serial dilutions of the serum from one-fourth to one one hundred twenty-eighths were used.

Compounds were tested for their ability to reduce the diameter of the wheals at the injection sites of dilutions of antibody which on all the controls have less than maximum response. Amounts of the compounds were administered to rats by subcutaneous injection, into the nuchal region, of a solution of the compound in P.B.S. or as a suspension in 1% methyl cellulose, each amount to a test group of six animals at a specified time prior to intravenous challenge with ovalbumin. The diameters of the blue wheals which developed on the tests group of animals were compared with those on a control group of six animals treated in the same way as the test group, but which had received an equivalent subcutaneous injection of the carrier fluid not containing the same volume of the compound under test.

% Inhibition of P.C.A. = $100 (1 - (a/b))$ $a$ = The mean of the sum of the diameters of the wheals produced in the test group of animals at those antibody sites where all the control group of animals gave less than maximum response.

$b$ = The mean of the sum of diameters of the wheals produced in the control group of animals at those antibody sites where all the animals in the group gave less than maximum response.

The preferred method of administration was a solution of the test compound dissolved in pH 7.2 buffer and neutralised with sodium bicarbonate. For those compounds having insoluble sodium salts, the salts were isolated by reaction of the free nitro compound with 2.5N sodium hydroxide and the filtered sodium salt washed free of alkali with water. The dried salts were then administered as a suspension in 1% methyl cellulose.

| PRODUCT OF EXAMPLE | STRUCTURE | RESULTS IN RAT PCA TEST | | |
|---|---|---|---|---|
| | | dose (mg/kg) | time (mins) | % inhibition of PCA response |
| Example 1 | benzene ring with $COCH_2NO_2$ and $CO_2Me$ | 25 / 100 / 25 / 100 | 0 / 0 / 60 / 60 | 0 / 12 / 32 / 23 |
| Example 2 | benzene ring with $COCH_2NO_2$ and $CO_2Et$ | 25 / 100 / 25 / 100 | 0 / 0 / 60 / 60 | 22 / 34 / 57 / 58 |
| Example 3 | Me, Me-substituted benzene with $COCH_2NO_2$ and $CO_2Me$ | 25 / 100 / 25 / 100 | 0 / 0 / 60 / 60 | 22 / 34 / 51 / 58 |
| Example 4 | Me, Me-substituted benzene with $COCH_2NO_2$ and $CO_2Et$ | 25 / 100 / 25 / 100 | 0 / 0 / 60 / 60 | 12 / 16 / 53 / 42 |
| Example 5 | Me, Me-substituted benzene with $COCH_2NO_2$ and $CO_2Pr^n$ | 25 / 100 / 25 / 100 | 0 / 0 / 60 / 60 | 7 / 11 / 44 / 54 |
| Example 6 | Me, Me-substituted benzene with $COCH_2NO_2$ and $CO_2Pr^i$ | 25 / 100 / 25 / 100 | 0 / 0 / 30 / 30 | 16 / 30 / 20 / 41 |
| Example 7 | Ph-substituted benzene with $COCH_2NO_2$ and $CO_2Me$ | 25 / 100 / 25 / 100 | 0 / 0 / 60 / 60 | 8 / 14 / −13 / −2 |
| Example 8 | benzene with $COCH_2NO_2$ and $CO_2H$ | 25 / 100 / 25 / 100 | 0 / 0 / 30 / 30 | 12 / 48 / 18 / 37 |
| Example 9 | Me, Me-substituted benzene with $COCH_2NO_2$ and $CO_2H$ | 25 / 100 / 25 / 100 | 0 / 0 / 60 / 60 | 33 / 57 / 13 / 32 |

| PRODUCT OF EXAMPLE | STRUCTURE | RESULTS IN RAT PCA TEST | | |
|---|---|---|---|---|
| | | dose (mg/kg) | time (mins) | % inhibition of PCA response |
| Example 10 | 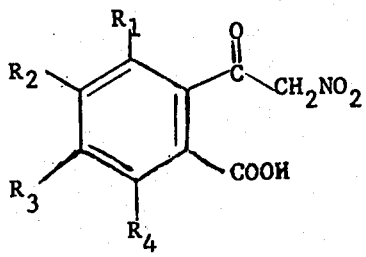 | 25 | 0 | 2 |
| | | 84 | 0 | 23 |
| | | 25 | 30 | 11 |
| | | 84 | 30 | 21 |

We claim:

1. A pharmaceutical composition in a dosage unit form suitable for oral, parenteral or insufflation administration to humans which comprises an amount of a compound of the formula (I)

$$\text{structure with } R_1, R_2, R_3, R_4 \text{ substituents, } CH_2NO_2 \text{ and } COOH \text{ groups}$$

a pharmaceutically acceptable non-toxic salt thereof or an ester thereof selected from the group consisting of lower alkyl, phenyl, benzyl, indanyl and phthalidyl esters, wherein $R_1$, $R_2$, $R_3$ and $R_4$ are the same or different and each is hydrogen, lower alkyl, lower alkoxy, phenyl, benzyl or halogen or any two of $R_1$, $R_2$, $R_3$ and $R_4$ taken together with the carbon atoms to which they are attached, form a phenyl, cyclohexyl or cyclohexenyl ring, sufficient to be effective for the prophylaxis of asthma, hayfever, or rhinitis in combination with a pharmaceutically acceptable non-toxic inert solid or syrupy carrier for oral administration, sterile liquid carrier for parenteral administration or a carrier for insufflation administration.

2. A pharmaceutical composition according to claim 1 wherein $R_1$, $R_2$, $R_3$ and $R_4$ are hydrogen, methyl, ethyl, n- or iso-propyl, n-, sec-, or tert-butyl, methoxy, ethoxy, n- or iso-propoxy, n-, sec- or tert-butoxy, phenyl, benzyl, fluoro, chloro, bromo or iodo.

3. A pharmaceutical composition according to claim 1 wherein $R_1$ and $R_2$ are both hydrogen, and $R_2$ and $R_3$ are methyl, ethyl or n-propyl.

4. A pharmaceutical composition according to claim 1 wherein two of $R_1$, $R_2$, $R_3$ and $R_4$ taken together, with the carbon atoms to which they are attached, form a phenyl, cyclohexyl or cyclohexenyl ring.

5. A pharmaceutical composition according to claim 1 wherein the compound of formula (I) is present in the form of said ester.

6. A pharmaceutical composition according to claim 5 wherein the ester is a lower alkyl ester.

7. A pharmaceutical composition according to claim 6 wherein the ester is a methyl, ethyl or n-propyl ester.

8. A pharmaceutical composition according to claim 5 wherein the ester is the phthalidyl ester.

9. A pharmaceutical composition according to claim 1 wherein the compound of formula (I) is present in the form of said salt.

10. A pharmaceutical composition according to claim 9 wherein the salt is the sodium salt.

11. A pharmaceutical composition according to claim 1 wherein the compound is 4,5-dimethyl-2-carboxy-ω-nitroacetophenone a pharmaceutically acceptable salt thereof, or the methyl or ethyl ester thereof.

12. A pharmaceutical composition according to claim 1 which is in the form of a microfine powder for insufflation.

13. A pharmaceutical composition according to claim 12 which additionally contains a small amount of a bronchodilator.

14. A pharmaceutical composition according to claim 13 wherein the bronchodilator is isoprenaline.

15. A pharmaceutical composition according to claim 1 wherein the carrier is a sterile liquid carrier for injection.

16. A pharmaceutical composition according to claim 1 in the form of a pill, tablet, capsule or powder which is suitable for mixing with water to form a syrup.

17. A pharmaceutical composition according to claim 1 wherein the compound is 4-ethyl-5-methyl-2-carboxy-ω-nitroacetophenone, or a pharmaceutically acceptable salt thereof, or the methyl or ethyl ester thereof.

18. A pharmaceutical composition according to claim 1 wherein the compound is 4,5-diethyl-2-carboxy-ω-nitroacetophenone, or a pharmaceutically acceptable salt thereof, or the methyl or ethyl ester thereof.

19. A pharmaceutical composition according to claim 1 wherein the compound is 4-methyl-5-ethyl-2-carboxy-ω-nitroacetophenone, or a pharmaceutically acceptable salt thereof, or the methyl or ethyl ester thereof.

20. A pharmaceutical composition according to claim 1 wherein the compound is 4,5-di-n-propyl-2-carboxy-ω-nitroacetophenone, or a pharmaceutically acceptable salt thereof, or the methyl or ethyl ester thereof.

21. A pharmaceutical composition according to claim 1 wherein the compound is 2-methoxy-carbonyl-ω-nitroacetophenone.

22. A pharmaceutical composition according to claim 1 wherein the compound is 2-ethoxycarbonyl-ω-nitroacetophenone.

23. A pharmaceutical composition according to claim 1 wherein the compound is 2-methoxycarbonyl-4,5-dimethyl-ω-nitroacetophenone.

24. A pharmaceutical composition according to claim 1 wherein the compound is 2-ethoxycarbonyl-4,5-dimethyl-ω-nitroacetophenone.

25. A pharmaceutical composition according to claim 1 wherein the compound is 2-n-propoxycarbonyl-4,5-dimethyl-ω-nitroacetophenone.

26. A pharmaceutical composition according to claim 11 wherein the compound is 2-isopropoxycarbonyl-4,5-dimethyl-ω-nitroacetophenone.

27. A pharmaceutical composition according to claim 1 wherein the compound is 2-methoxycarbonyl-5-phenyl-ω-nitroacetophenone.

28. A pharmaceutical composition according to claim 1 wherein the compound is 2-methoxycarbonyl-3-phenyl-ω-nitroacetophenone.

29. A pharmaceutical composition according to claim 1 wherein the compound is ω-nitroacetophenone-2-carboxylic acid.

30. A pharmaceutical composition according to claim 1 wherein the compound is ω-nitro-3-phenylacetophenone-2-carboxylic acid.

31. A method for the prophylaxis of asthma, hayfever and rhinitis in humans which comprises administering to a human in need thereof orally, parenterally or by insufflation an amount of a compound of the formula:

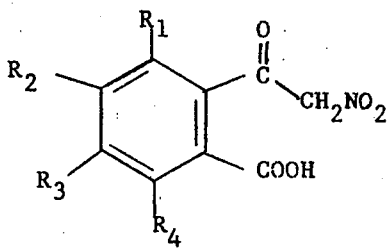

a pharmaceutically acceptable non-toxic salt thereof or an ester thereof selected from the group consisting of lower alkyl, phenyl, benzyl, indanyl and phthalidyl esters, wherein $R_1$, $R_2$, $R_3$ and $R_4$ are the same or different and each is hydrogen, lower alkyl, lower alkoxy, phenyl, benzyl or halogen or any two of $R_1$, $R_2$, $R_3$ and $R_4$ taken together with the carbon atoms to which they are attached, form a phenyl, cyclohexyl or cyclohexenyl ring, sufficient to be effective for the prophylaxis of asthma, hayfever, or rhinitis, in combination with a pharmaceutically acceptable non-toxic inert carrier, for said administration form.

32. A method according to claim 31 wherein $R_1$, $R_2$, $R_3$ and $R_4$ are hydrogen, methyl, ethyl, n- or iso-propyl, n-, sec-, or tert-butyl, methoxy, ethoxy, n- or isopropoxy, n-, sec- or tert-butoxy, phenyl, benzyl, fluoro, chloro, bromo or iodo.

33. A method according to claim 31 wherein $R_1$ and $R_2$ are both hydrogen, and $R_2$ and $R_3$ are methyl, ethyl or n-propyl.

34. A method according to claim 31 wherein two of $R_1$, $R_2$, $R_3$ and $R_4$ taken together, with the carbon atoms to which they are attached, form a phenyl, cyclohexyl or cyclhexenyl ring.

35. A method according to claim 31 wherein the compound of formula (I) is present in the form of said ester.

36. A method according to claim 35 wherein the ester is a lower alkyl ester.

37. A method according to claim 36 wherein the ester is a methyl, ethyl or n-propyl ester.

38. A method according to claim 35 wherein the ester is the phthalidyl ester.

39. A method according to claim 31 wherein the compound of formula (I) is present in the form of said salt.

40. A method according to claim 39 wherein the salt is the sodium salt.

41. A method according to claim 31 wherein the administration is by insufflation.

42. A method according to claim 41 wherein the composition additionally contains a small amount of a bronchodilator and the administration is by insufflation.

43. A method according to claim 42 wherein the bronchodilator is isoprenaline.

44. A method according to claim 31 wherein the administration is by injection.

45. A method according to claim 31 wherein the administration is oral.

46. A method according to claim 36 wherein the compound is 4-ethyl-5-methyl-2-carboxy-ω-nitroacetophenone, or a pharmaceutically acceptable salt thereof, or the methyl or ethyl ester thereof.

47. A method according to claim 31 wherein the compound is 4,5-diethyl-2-carboxy-ω-nitroacetophenone, or a pharmaceutically acceptable salt thereof, or the methyl or ethyl ester thereof.

48. A method according to claim 31 wherein the compound is 4-methyl-5-ethyl-2-carboxy-ω-nitroacetophenone, or a pharmaceutically acceptable salt thereof, or the methyl or ethyl ester thereof.

49. A method according to claim 31 wherein the compound is 4,5-di-n-propyl-2-carboxy-ω-nitroacetophenone, or a pharmaceutically acceptable salt thereof, or the methyl or ethyl ester thereof.

50. A method according to claim 31 wherein the compound is 2-methoxy-carbonyl-ω-nitroacetophenone.

51. A method according to claim 31 wherein the compound is 2-ethoxycarbonyl-ω-nitroacetophenone.

52. A method according to claim 31 wherein the compound is 2-methoxycarbonyl-4,5-dimethyl-ω-nitroacetophenone.

53. A method according to claim 31 wherein the compound is 2-ethoxycarbonyl-4,5-dimethyl-ω-nitroacetophenone.

54. A method according to claim 31 wherein the compound is 2-n-propoxycarbonyl-4,5-dimethylω-nitroacetophenone.

55. A method according to claim 31 wherein the compound is 2-isopropoxycarbonyl-4,5-dimethyl-ω-nitroacetophenone.

56. A method according to claim 31 wherein the compound is 2-methoxycarbonyl-5-phenylω-nitroacetophenone.

57. A method according to claim 31 wherein the compound is 2-methoxycarbonyl-3-phenyl-ω-nitroacetophenone.

58. A method according to claim 31 wherein the compound is ω-nitroacetophenone-2-carboxylic acid.

59. A method according to claim 31 wherein the compound is ω-nitro-3-phenylacetophenone-2-carboxylic acid.

60. A method according to claim 31 wherein the compound and the carrier are in the form of a microfine powder and the administration is by insufflation.

61. A method according to claim 60 wherein the compound and the carrier additionally contain a small amount of a bronchodilator.

62. A method according to claim 60 wherein the bronchodilator is isoprenaline.

63. A method according to claim 31 wherein the compound and the carrier are in the form of a pill, a tablet, or a capsule, or a powder which is suitable for mixing with water to form a syrup and the administration is oral.

* * * * *